(12) United States Patent
Sharratt et al.

(10) Patent No.: US 9,012,703 B2
(45) Date of Patent: Apr. 21, 2015

(54) PROCESS FOR PURIFYING (HYDRO) FLUOROALKENES

(75) Inventors: Andrew P Sharratt, Cheshire (GB); Claire E McGuiness, Cheshire (GB); John Hayes, Cheshire (GB)

(73) Assignee: Mexichem Amanco Holdings S.A. de C.V., Tlalnepantla (MX)

( * ) Notice: Subject to any disclaimer, the term of this patent is extended or adjusted under 35 U.S.C. 154(b) by 109 days.

(21) Appl. No.: 13/502,278

(22) PCT Filed: Oct. 8, 2010

(86) PCT No.: PCT/GB2010/001879
§ 371 (c)(1),
(2), (4) Date: Apr. 16, 2012

(87) PCT Pub. No.: WO2011/045559
PCT Pub. Date: Apr. 21, 2011

(65) Prior Publication Data
US 2012/0203037 A1 Aug. 9, 2012

(30) Foreign Application Priority Data
Oct. 15, 2009 (GB) .................. 0918069.6

(51) Int. Cl.
*C07C 17/389* (2006.01)
*C07C 21/18* (2006.01)

(52) U.S. Cl.
CPC .................. *C07C 17/389* (2013.01)

(58) Field of Classification Search
USPC .............................. 570/177, 179
See application file for complete search history.

(56) References Cited

U.S. PATENT DOCUMENTS

| 6,110,436 | A * | 8/2000 | Scholz et al. .............. 423/240 S |
| 2003/0157009 | A1 | 8/2003 | Corr et al. |
| 2011/0105809 | A1 | 5/2011 | Devic et al. |

FOREIGN PATENT DOCUMENTS

| CN | 101351429 | | 1/2009 |
| GB | 2439209 | | 12/2007 |
| JP | S64-040436 | | 2/1989 |
| JP | S64-040507 | | 2/1989 |
| JP | 2002154996 | | 5/2002 |
| JP | 2003261480 | | 9/2003 |
| JP | 2003335712 | | 11/2003 |
| JP | 2006-156539 | | 6/2006 |
| JP | 2010/0180134 | | 8/2010 |
| WO | WO94/00382 | | 1/1994 |
| WO | WO 9400382 | A1 * | 1/1994 |
| WO | WO01/83411 | | 11/2001 |
| WO | WO2007/123786 | | 11/2007 |
| WO | WO2008/001844 | | 1/2008 |
| WO | WO2008/008695 | | 1/2008 |
| WO | WO 2008001844 | A1 * | 1/2008 |
| WO | WO2010/001025 | | 1/2010 |

OTHER PUBLICATIONS

Ohno, H. et al. Patent No. WO2008/001844, Abstract English translation.*
Ohno, H. et al. Patent No. WO2008/001844, Full English translation.*
Ohno, H. et al. Patent No. WO2008/001844, English translation mailed on Oct. 31, 2013.*
Hayashi et al., Purification of hexafluoropropylene, Chemical Abstracts, 111, No. 7, Aug. 14, 1989.
http://en/wikipedia.org/wiki/Acitvated_Carbon, retrieved Sep. 29, 2009.
http://wikipedia.org/wiki/Molecular_sieve, retireved Sep. 29, 2009.
http://www.asge-online.com/AdsbMSievespg175.html, retrieved Sep. 17, 2009.
Zhou et al., Structures and Transformation Mechanisms of the n, y and 0 Transition Aluminas, Acta Cryst., B47, 617-630, 1991.
Ohno, H. et al., WIPO Publication WO 2008/001844 of PCT Application PCT/JP2007/062995, Full English Translation, Jan. 3, 2008.

* cited by examiner

*Primary Examiner* — Fereydoun G Sajjadi
*Assistant Examiner* — Medhanit Bahta
(74) *Attorney, Agent, or Firm* — Ryan Kromholz & Manion, S.C.

(57) ABSTRACT

The invention relates to a process for removing one or more undesired (hydro)halocarbon compounds from a (hydro)fluoroalkene, the process comprising contacting a composition comprising the (hydro)fluoroalkene and one or more undesired (hydro)halocarbon compounds with an aluminum-containing absorbent, activated carbon, or a mixture thereof.

29 Claims, No Drawings

PROCESS FOR PURIFYING (HYDRO) FLUOROALKENES

The invention relates to a process for purifying (hydro) fluoroalkenes.

The listing or discussion of background information or an apparently prior-published document in this specification should not necessarily be taken as an acknowledgement that the information or document is part of the state of the art or is common general knowledge.

(Hydro)fluoroalkenes are increasingly being considered as working fluids in applications such as refrigeration, heat pumping, foam blowing, fire extinguishers/retardants, propellants and solvency (e.g. plasma cleaning and etching). The processes used to make (hydro)fluoroalkenes can lead to the generation of toxic and/or otherwise undesirable by-products. The presence of small quantities of impurities may not be detrimental to the bulk physical properties of the (hydro) fluoroalkene product and for some applications their removal is unnecessary. However, some applications require very low levels of impurities, and many of these are difficult to remove from the (hydro)fluoroalkenes by recognized means.

For instance, impurities are often removed from (hydro) fluoroalkenes by distillation, but this method of removal is made difficult if the boiling point of the impurity is close to that of the (hydro)fluoroalkene or if substance interactions bring otherwise dissimilar boiling compounds close together (for example azeotropes). Furthermore, even after distillation, it is possible that small quantities of undesirable impurities will remain.

3,3,3-trifluoropropene (R-1243zf) is an example of a (hydro)fluoroalkene. R-1243zf is believed to find use in applications such as refrigeration. Commercially available R-1243zf contains many impurities, including the highly toxic species 1,2,3,3,3-pentafluoropropene (R-1225ye), 1,1,3,3,3-pentafluoropropene (R-1225zc), and the chlorofluorocarbon species chlorofluoromethane (R-31), chlorofluoroethene (R-1131), trichlorofluoromethane (R-11), dichlorodifluoromethane (R-12), chlorotrifluoromethane (R-13), and dichlorotetrafluoroethane (R-114) that are damaging to the environment. Distillation is of limited use in purifying R-1243zf because it is difficult to remove all the impurities using this technique. For example, R-1225zc (boiling point −25.82° C.) is very difficult to remove from R-1243zf (boiling point −25.19° C.) by distillation.

In summary, there is a need for an improved method for purifying (hydro)fluoroalkenes.

The inventors have surprisingly found that an aluminium-containing absorbent, activated carbon, or a mixture thereof, is effective at removing one or more undesired (hydro)halocarbon compounds from a composition also containing a desired (hydro)fluoroalkene.

Thus, the subject invention addresses the foregoing and other deficiencies by providing a process for removing one or more undesired (hydro)halocarbon compounds from a (hydro)fluoroalkene, the process comprising contacting a composition comprising the (hydro)fluoroalkene and one or more undesired (hydro)halocarbon compounds with an aluminium-containing absorbent, activated carbon, or a mixture thereof.

By term "(hydro)fluoroalkenes", we are referring to straight-chain or branched unsaturated compounds that contain fluorine and optionally hydrogen atoms in addition to carbon atoms. Thus, the term includes perfluoroalkenes as well as hydrofluoroalkenes which contain both fluorine and hydrogen atoms in addition to carbon. Hydrofluoroalkenes are a preferred group of (hydro)fluoroalkenes. Preferred examples of (hydro)fluoroalkenes include $C_{2-10}$ (hydro)fluoroalkenes, and particularly $C_{3-7}$ (hydro)fluoroalkenes. In one embodiment, the (hydro)fluoroalkene is a $C_{3-7}$ hydrofluoroalkene which contains hydrogen and fluorine substituents.

In a preferred embodiment, the (hydro)fluoroalkene is a (hydro)fluoropropene. Examples of (hydro)fluoropropenes which may be purified by the process of the invention include those containing contain 0, 1, 2, 3, 4 or 5 hydrogen substituents and 1, 2, 3, 4, 5 or 6 fluorine substituents. Preferred (hydro)fluoropropenes are hydrofluoropropenes having from 3 to 5 fluorine atoms (and thus from 1 to 3 hydrogen atoms). In other words, preferred hydrofluoropropenes are trifluoropropenes, tetrafluoropropenes and pentafluoropropenes, particularly trifluoropropenes and tetrafluoropropenes.

Examples of suitable trifluoropropenes include but are not limited to 3,3,3-trifluoropropene ($CF_3CH=CH_2$, also known as R-1243zf), 2,3,3-trifluoropropene ($CF_2HCF=CH_2$), 1,2,3-trifluoropropene ($CFH_2CF=CHF$) and 1,3,3-trifluoropropene ($CF_2HCH=CHF$). A preferred trifluoropropene which can be purified by the process of the invention is R-1243zf.

Examples of suitable tetrafluoropropenes include 2,3,3,3-tetrafluoropropene ($CF_3CF=CH_2$, also known as R-1234yf), 1,3,3,3-tetrafluoropropene (E/Z-$HFC=CHCF_3$, also known as R-1234ze), 1,2,3,3-tetrafluoropropene ($HFC=CFCF_2H$), 1,1,3,3-tetrafluoropropene ($F_2C=CHCF_2H$) and 1,1,2,3-tetrafluoropropene ($F_2C=CFCH_2F$). R-1234ze and R-1234yf are preferred tetrafluoropropenes that can be purified by the process of the invention, particularly R-1234ze.

Examples of suitable pentafluoropropenes include 1,2,3,3,3-pentafluoropropene (E/Z-$HFC=CFCF_3$, also known as R-1225ye), 1,1,3,3,3-pentafluoropropene ($F_2C=CHCF_3$, also known as R-1225zc) and 1,1,2,3,3-pentafluoropropene ($F_2C=CFCF_2H$). Of these, R-1225ye is a preferred pentafluoropropene which can be purified by the process of the invention.

In one embodiment, the (hydro)fluoroalkene which may be purified by the process of the invention is a hydrofluoropropene selected from R-1243zf, R-1234yf, R-1234ze, R-1225ye and mixtures thereof. Preferably, the (hydro)fluoroalkene is selected from R-1243zf, R-1234yf, R-1234ze and mixtures thereof, such as selected from R-1243zf and/or R-1234yf, or selected from R-1243zf and/or R-1234ze.

By the term "undesired (hydro)halocarbon compounds", we mean any saturated or unsaturated straight-chain or branched compounds containing halogen and optionally hydrogen atoms in addition to carbon atoms that it is desirable to remove from the (hydro)fluoroalkene which is being purified. Thus, the term includes perhalocarbons as well as hydrohalocarbons which contain both hydrogen and halogen atoms in addition to carbon atoms. Typically, this includes (hydro) fluoroalkanes, (hydro)fluoroalkenes (hydro)fluoroalkynes and (hydro)chlorofluorocarbon (CFC) species such as (hydro)chlorofluoroalkanes, (hydro)chlorofluoroalkenes, and (hydro)chlorofluoroalkynes.

The undesired (hydro)halocarbon compounds described above can include (hydro)fluoroalkenes. The skilled person would understand that certain undesired (hydro)fluoroalkenes can be present in a composition containing a desired (hydro)fluoroalkene. Examples of such undesired (hydro)fluoroalkenes may include those containing a $=CHF$ or $=CF_2$ group. The inventors have unexpectedly found that an aluminium-containing absorbent, activated carbon, or a mixture thereof, can be effective at removing (hydro)fluoroalkenes containing a $=CHF$ or $=CF_2$ moiety (especially $=CF_2$) from a composition containing a desired (hydro)fluoroalkene.

By way of example, if the skilled person is attempting to purify a particular trifluoropropene (e.g. R-1243zf), that trifluoropropene may be contaminated by other (hydro)fluoroalkenes, such as tetrafluoropropenes or pentafluoropropenes. As noted above, R-1225ye and R-1225zc are typical impurities in commercially available R-1243zf. By use of an aluminium-containing absorbent and/or activated carbon, such undesired (hydro)fluoroalkenes may be removed from a composition containing a desired (hydro)fluoroalkene by the process of the invention. Accordingly, in one embodiment, the desired (hydro)fluoroalkene (e.g. (hydro)fluoropropene) that is purified by the process of the invention is not (i) a pentafluoropropene, such as R-1225ye, R-1225zc, or $F_2C=CFCF_2H$ (e.g. R-1225zc); or (ii) a (hydro)fluoroalkene containing a $=CF_2$ moiety.

In one aspect, the process of the invention is effective at removing the undesired (hydro)halocarbon(s) R-1225zc, R-31, and/or R133a from a composition comprising the desired (hydro)fluoroalkene R-1243zf.

Alternatively or additionally, the process of the invention is effective at removing the undesired (hydro)halocarbon trifluoromethylacetylene (TFMA) from a composition comprising the desired (hydro)fluoroalkene R-1234ze.

Either the aluminium-containing absorbent or activated carbon may be porous or non-porous, but preferably porous.

A preferred aluminium-containing adsorbent for use in processes according to the invention is an alumina or alumina-containing substrate. Advantageously, the substrate is porous. Further information on the various crystalline forms of alumina can be found in Acta. Cryst., 1991, B47, 617, the contents of which are hereby incorporated by reference.

Preferred aluminium-containing adsorbents (e.g. alumina) for use according to the invention will have functionality that facilitates their combination with the compounds the adsorbent is removing. Examples of such functionality include acidity or basicity, which can be Lewis-type or Bronsted-type in nature, which will facilitate its combination with the compounds the adsorbent is removing. The acidity or basicity can be modified in a manner well known to those skilled in the art by using modifiers such as sodium sulphate. Examples of aluminium-containing adsorbents with acidic or basic functionality include Eta-alumina, which is acidic, and Alumina AL0104, which is basic.

Aluminosilicate molecular sieves (zeolites) are a further preferred group of aluminium-containing adsorbent that may be used in the subject invention. Typically, the zeolites have pores having openings which are sufficiently large to allow the desired and undesired compounds to enter into the interior of the zeolite whereby the undesired compounds are retained. Accordingly, zeolites having pores which have openings which have a size across their largest dimension in the range of 3 Å to 12 Å are preferred.

Preferred zeolites have a pore opening sufficiently large to allow the undesired compounds to enter into the interior of the zeolite whereby the undesired compounds are retained, whilst excluding the desired compound from entering the interior of the zeolite. Such zeolites typically have openings which have a size across their largest dimension in the range of 3 Å to 12 Å, preferably from 3 Å to 10 Å or 4 Å to 12 Å. Particularly preferred are those molecular sieves having pores which have openings having a size across their largest dimension in the range of 4 Å to 10 Å, such as 4 Å to 8 Å (e.g. 4 Å to 5 Å) and may include zeolite Y, ultra-stable Y (dealuminated-Y), zeolite beta, zeolite X, zeolite A and zeolite ZSM-5, AW-500.

By opening in this context we are referring to the mouth of the pore by which the undesired compound enters the body of the pore, where it may be retained. The openings to the pores may be elliptically shaped, essentially circular or even irregularly shaped, but will generally be elliptically shaped or essentially circular. When the pore openings are essentially circular, they should have a diameter in the range of about 3 Å across their smaller dimension. They can still be effective at adsorbing compounds provided that the size of the openings across their largest dimension is in the range of from about 3 Å to about 12 Å. Where the adsorbent has pores having elliptically shaped openings, which are below 3 Å across their smaller dimension, they can still be effective at adsorbing compounds provided that the size of the openings across their largest dimension is in the range of from about 3 Å to about 12 Å.

By "activated carbon", we include any carbon with a relatively high surface area such as from about 50 to about 3000 $m^2$ or from about 100 to about 2000 $m^2$ (e.g. from about 200 to about 1500 $m^2$ or about 300 to about 1000 $m^2$). The activated carbon may be derived from any carbonaceous material, such as coal (e.g. charcoal), nutshells (e.g. coconut) and wood. Any form of activated carbon may be used, such as powdered, granulated, extruded and pelleted activated carbon.

Activated carbon is preferred which has been modified (e.g. impregnated) by additives which modify the functionality of the activated carbon and facilitate its combination with the compounds it is desired to removed. Examples of suitable additives include metals or metal compounds, and bases.

Typical metals include transition, alkali or alkaline earth metals, or salts thereof. Examples of suitable metals include Na, K, Cr, Mn, Au, Fe, Cu, Zn, Sn, Ta, Ti, Sb, Al, Co, Ni, Mo, Ru, Rh, Pd and/or Pt and/or a compound (e.g. a halide, hydroxide, carbonate) of one or more of these metals. Alkali metal (e.g. Na or K) salts are currently a preferred group of additive for the activated carbon, such as halide, hydroxide or carbonate salts of alkali metals salts. Hydroxide or carbonate salts of alkali metals salts are bases. Any other suitable bases can be used, including amides (e.g. sodium amide).

The impregnated activated carbon can be prepared by any means known in the art, for example soaking the carbon in a solution of the desired salt or salts and evaporating the solvent.

Examples of suitable commercially available activated carbons include those available from Chemviron Carbon, such as Carbon 207C, Carbon ST1X, Carbon 209M and Carbon 207EA. Carbon ST1X is currently preferred. However, any activated carbon may be used with the invention, provided they are treated and used as described herein.

Advantageously, a combination of an aluminium-containing absorbent and activated carbon is used in the process of the invention, particularly when each are separately effective at removing particular undesired compounds from a composition also containing a desired (hydro)fluoroalkene. Examples of preferred combinations of aluminium-containing absorbent and activated carbon include zeolite and activated carbon and aluminium-containing absorbent and impregnated activated carbon.

The invention may be applied to any composition containing a (hydro)fluoroalkene from which it is desired to remove one or more undesired (hydro)halocarbon compounds. For example, the composition may be a product stream from a process for producing the (hydro)fluoroalkene. Accordingly, the process of the invention may be a purification step in a process for producing the (hydro)fluoroalkene.

The process of the invention may be one of several purification steps in a process for producing the fluoroalkene. For example, the process of the invention may be combined with one or more distillation, condensation or phase separation steps and/or by scrubbing with water or aqueous base.

The process of the invention requires the composition (e.g. product stream) to be in the liquid or vapour phase. Liquid phase contacting is preferred.

Processing with a stationary bed of the adsorbent will typically be applied to continuous processes. The composition (e.g. product stream) is passed over or through the stationary bed comprising the aluminium-containing absorbent, activated carbon, or a mixture thereof.

The aluminium-containing absorbent, activated carbon, or a mixture thereof is normally pre-treated prior to use by heating in a dry gas stream, such as dry air or dry nitrogen. This process has the effect of activating the aluminium-containing absorbent, activated carbon, or a mixture thereof. Typical temperatures for the pre-treatment are in the range of from about 100 to about 400° C. (e.g. about 100 to about 300° C.).

The process of the invention can be operated in a batch or continuous manner, although a continuous manner is preferred. In either case, during operation of the process, the absorption capability of the aluminium-containing absorbent, activated carbon, or a mixture thereof is gradually reduced as the pores become occupied with the one or more undesired (hydro)halocarbon compounds. Eventually, the ability of the aluminium-containing absorbent, activated carbon, or a mixture thereof to absorb the undesired compound(s) will be substantially impaired, at which stage it should be regenerated. Regeneration is typically effected by heating the used aluminium-containing absorbent, activated carbon, or a mixture thereof in a dry gas stream, such as dry air or dry nitrogen, at a temperature in the range of from about 100 to about 400° C., such as from about 100 to about 300° C. (e.g. about 100 to about 200° C.), and a pressure in the range of from about 1 to about 30 bar (e.g. about 5 to about 15 bar).

The process of the invention typically is conducted at a temperature in the range of from about −50° C. to about 200° C., preferably from about 0° C. to about 100° C., such as from about 10 to about 50° C. This temperature range applies to the temperature of the interior of the purification vessel.

(Hydro)fluoroalkenes contain a double bond which is susceptible to reaction, particularly when contacted with aluminium-containing absorbent and/or activated carbon containing reactive functionality (e.g. acid, base, metal etc). For example, certain (hydro)fluoroalkenes are known to be monomers, and one might expect them to polymerise in the presence of such absorbents.

The inventors have found that the (hydro)fluoroalkenes are surprisingly stable in the presence of aluminium-containing absorbent and/or activated carbon. This may be in part due to the mild conditions (e.g. temperature) under which the process of the invention can be carried out.

Typical operating pressures for the process of the invention are from about 1 to about 30 bar, such as from about 1 to about 20 bar, preferably from about 5 to about 15 bar.

In the (batch) process of the invention, the aluminium-containing absorbent, activated carbon, or a mixture thereof typically is used in an amount of from about 0.1 to about 100% by weight, such as from about 1 or 5 to about 50% by weight, preferably from about 10 to about 50% by weight, based on the weight of the composition comprising the (hydro)fluoroalkene and one or more undesired compounds.

In a continuous process of the invention, the typical feed rate of the composition (e.g. product stream) comprising the (hydro)fluoroalkene and one or more undesired compounds to the aluminium-containing absorbent, activated carbon, or a mixture thereof is such that in the liquid phase the contact time of the adsorbate with the adsorbent is from about 0.1 to 24 hours, preferably from about 1 to 8 hours. In a preferred mode of operation the adsorbate is continuously recycled through the adsorbent bed until the level of the undesired components has reduced sufficiently, Where vapour phase contacting is utilised, the contact time of the adsorbate with the adsorbent is from about 0.001 to 4 hours, preferably from about to 0.01 to 0.5 hours. In a preferred mode of operation the adsorbate is continuously recycled through the adsorbent bed until the level of the undesired components has reduced sufficiently.

The invention is particularly suitable for removing relatively low levels of undesired (hydro)halocarbon compound(s) from the composition (e.g. product stream) containing the (hydro)fluoroalkene being purified. Typical levels are from about 0.1 to about 1000 ppm, such as from about 0.1 to about 500 ppm, preferably from about 1 to about 100 ppm.

The process of the invention removes at least a portion of undesired (hydro)halocarbon compound(s) present in the composition comprising the desired (hydro)fluoroalkene. Preferably, the invention removes at least 50%, 60%, 70% or 80% of the undesired compound(s) present in the composition comprising the desired (hydro)fluoroalkene. More preferably, the composition removes at least 90%, 95% or even 99% of the undesired compound(s) present in the composition comprising the desired (hydro)fluoroalkene.

Following purification by the process of the invention, the level of undesired compound(s) in the composition comprising the desired (hydro)fluoroalkene typically will be from not detectable (by currently available techniques, such as capillary gas chromatography) to about 10 ppm, such as from about 0.01 ppm to about 5 ppm, preferably from not detectable to about 1 ppm.

The invention is illustrated by the following non-limiting examples.

Example 1

A range of adsorbents were screened for their efficacy in removing the target compounds R-1225zc and trifluoromethylacetylene (TFMA) from R-1243zf. A sample of R-1243zf doped with 400 ppm wt/wt TFMA and 765 ppm wt/wt R-1225zc was prepared. 50 g of this R-1243zf was then treated with 5 g of adsorbent in a sealed pressure tube at ambient temperature. Samples were taken for analysis by capillary GC after 20 minutes and in some cases after 16 hours of contacting of the R-1243zf with the adsorbent. The following adsorbents were screened:

Eta-Alumina ex-BASF—an acidic form of activated alumina

Chemviron Activated Carbon 207EA

10% Potassium hydroxide on Chemviron Activated Carbon 207EA

10% Potassium carbonate on Chemviron Activated Carbon 207EA

10% Potassium Iodide on Chemviron Activated Carbon 207EA

10% Potassium Hydroxide and 10% Potassium Iodide on Chemviron Activated Carbon 207EA Chemviron ST1x—an activated carbon comprising 207EA impregnated with various species including base(s)

The doped samples of 207EA were prepared by aqueous impregnation. The dopant(s) (1 g) was/were dissolved in 100 g water and 10 g of 207EA added. After mixing the water was removed in vacuo to leave a free running solid.

Prior to use all adsorbents were pre-activated at 250-300° C. in a nitrogen purged oven for a minimum of 16 hours.

The results are presented in the Table below:

| Adsorbent | % Removal of contaminant (0% = no effect; 100% = complete removal) | | | |
|---|---|---|---|---|
| | 20 mins R-1225zc | 20 mins TFMA | 16 hrs R-1225zc | 16 hrs TFMA |
| 207EA Carbon & 10% KOH | 69 | 8 | 97 | 8 |
| 207EA Carbon & 10% K2CO3 | 41 | 4 | 58 | 29 |
| 207EA Carbon & 10% KI | 4 | 7 | — | — |
| 207EA Carbon | 4 | −1 | — | — |
| ST1x Impregnated Carbon | 46 | 9 | 100 | 31 |
| 207EA Carbon & 10% KOH & KI | 13 | 5 | 70 | 8 |
| Eta Alumina | 7 | 7 | 18 | 16 |

All of the adsorbents screened showed utility in removal of either or both of R-1225zc and TFMA from R-1243zf. However, the most effective adsorbents were those doped with base, either potassium hydroxide or carbonate, including the ST1x carbon.

Example 2

A sample of commercially available R-1243zf (this may be obtained from Apollo Scientific, for example) was obtained and analysed by capillary GC-MS. This R-1243zf was found to contain, amongst other, the following impurities:

| Impurity | PPM wt/wt | Boiling point ° C. |
|---|---|---|
| R-134a | 2.5 | −26.074 |
| R-1225zc | 7.4 | −25.82 |
| R-1234yf | 26 | −29.69 |
| R-134 | 87 | −23.15 |
| Z-R-1225ye | 0.8 | −19.3 |
| R-152a | 251 | −24.023 |
| R-40 | 0.9 | −24.15 |
| R-31 | 11 | −9.15 |
| R-133a | 2.3 | +7.51 |

R-1225zc, R-31 and R-133a are toxic compounds and it was considered desirable to remove them from the R-1243zf prior to use, for example as a refrigerant. Even where boiling point differences make the separation of some of these components from R-1243zf by distillation practicable, the low levels mean that such a process would be very energy intensive and inefficient. Therefore, an alternative means of removing these impurities, particularly the R-1225zc, R-31 and R-133a, from 1243zf was sought. To that end a series of experiments were performed in which the efficacy of a range of adsorbent materials for the removal of the three target compounds R-1225zc, R-31 and R-133a from R-1243zf was tested.

The range of adsorbents screened comprised:

Eta-Alumina ex-BASF—an acidic form of activated alumina

Chemviron Activated Carbon 207c—derived from coconut shells

Chemviron Activated Carbon 209M

Chemviron Activated Carbon 207EA

Chemviron ST1x—an activated carbon comprising 207EA impregnated with various species including base(s)

Chemviron Activated Carbon 209m

13× Molecular sieve—An aluminosilicate or Zeolite

AW500—An acid stable aluminosilicate or Zeolite

Alumina AL0104—ex BASF—a basic form of alumina

The carbon based adsorbents were pre-activated at 200° C. in flowing nitrogen for 16 hours prior to use and the inorganic adsorbents activated at 300° C. in flowing nitrogen again for 16 hours. The efficacy of each of the adsorbents was then assessed by treating c.a. 100 g of R-1243zf with 2-4 g of each adsorbent in a re-circulatory system whereby the R-1243zf was continuously pumped through the adsorbent bed for 16 hours at ambient temperature. After the treatment period a small sample of the R-1243zf was taken for analysis by capillary GC-MS. The analysis of the treated R-1243zf is compared with the untreated R-1243zf (see previous table for the amounts of impurities) in the following table.

| Adsorbent | Mass Adsorbent (g) | Mass R-1243zf (g) | R-134a (ppm wt/wt) | R-1225zc (ppm wt/wt) | R-1234yf (ppm wt/wt) | R-134 (ppm wt/wt) | Z-R-1225ye (ppm wt/wt) | R-152a (ppm wt/wt) | R-40 (ppm wt/wt) | R-31 (ppm wt/wt) | R-133a (ppm wt/wt) |
|---|---|---|---|---|---|---|---|---|---|---|---|
| Eta- Alumina | 2.0000 | 100 | 96 | 4.2 | 26 | 85 | 1 | 141 | 11 | 4.8 | 3 |
| Carbon 207C | 2.2879 | 92 | 3.6 | 7.9 | 28 | 93 | 1 | 231 | 4 | 11 | 1 |
| Carbon ST1X | 2.5165 | 109.3 | 3.1 | ND | 26 | 87 | 0.5 | 241 | 5.9 | 4.1 | ND |
| Carbon 209M | 2.6644 | 122.9 | 4.1 | 5.8 | 26 | 87 | 1 | 251 | 2.97 | 11 | 1.2 |
| 13-X Sieve | 3.9841 | 132 | 3.9 | 8 | 27 | 12 | 0.8 | 116 | ND | 2.4 | 1 |
| AW 500 | 3.8865 | 131.2 | 3.7 | 8.2 | 28 | 5 | 1.1 | 19 | 1 | ND | ND |
| BASF AL0104 | 4.3562 | 134.6 | 3.2 | ND | 25 | 85 | 0.8 | 236 | 0.9 | 8 | ND |
| Carbon 207 EA | 2.6738 | 118.1 | 2.4 | 6.8 | 25 | 84 | 0.8 | 222 | 1.1 | 11 | 2.2 |

All of the adsorbents tested were effective in reducing the level of at least one contaminant. However, for the three target compounds R-1225zc, R-31 and R-133a, the base impregnated activated carbon ST1x and molecular sieve AW500 were particularly effective.

Example 3

R-1243zf has previously found use as a monomer and as an olefin might reasonable be expected to be susceptible to polymerisation or other reactions particularly when contacted with reactive surfaces present in many of the absorbents used in the process of the invention. This would seriously limit the commercial applicability of this invention. Therefore, we sought to investigate whether any reaction processes accompanied the adsorptive purification of R-1243zf by contacting with absorbents such as ST1x carbon and AW500.

Samples of ST1x carbon and AW500 were pre-treated at 200-300° C. under flowing nitrogen for 16 hours prior to use.

20 g samples were then taken and accurately weighed and added to a clean, dry 300 ml Hastelloy autoclave either individually or together. The autoclave was sealed, purged with nitrogen and pressure tested. The autoclave was then charged with R-1243zf. The autoclave and its contents were then heated to either 80 or 120° C. for a period of 24 hours. At the end of each experiment, the R-1243zf was recovered for analysis. The adsorbent was also recovered and following drying at 105° C. was re-weighed. The results are presented in the Tables below.

At the end of each experiment the recovered R-1243zf was visually unchanged. There were no residues left behind upon evaporation of the R-1243zf following each test. The detailed analysis revealed that the adsorbents ST1x and AW500 either alone or particularly in combination were still effective under the conditions of these tests. Furthermore, there was no evidence for any undesirable side reactions including polymerisation or decomposition. Therefore these adsorbents alone and in combination were shown to be suitable for the purification of e.g. R-1243zf at commercial scale.

| | Feed Impurity | | | | | | | |
|---|---|---|---|---|---|---|---|---|
| | 227 ea | 134a | 1225zc | 1234vf | 134 | 1225ye-Z | 152a | $CH_3Cl$ |
| | Feed Impurity level ppm wt/wt | | | | | | | |
| | 5.1747 | 2.1878 | 7.6842 | 27.7435 | 78.5234 | 0.8828 | 266.3725 | 0.8193 |
| Stability test—Impurity levels post experiment | | | | | | | | |
| AW 500 Molecular sieve @ 80 deg autoclave ref. 65 | 0 | — | 4.7881 | 20.8933 | 9.3329 | 1.8548 | 58.2016 | 0 |
| AW 500 Molecular sieve sieve @ 80 deg autoclave ref 66 | 0 | 66.0333 | 8.4049 | 28.4736 | 9.4839 | 0.911 | 50.6359 | 0 |
| AW 500 Molecular sieve@ 120 deg autoclave ref 65 | 0 | 107.839 | 6.3199 | 26.1201 | 9.6007 | 0.8829 | 35.9887 | 0 |
| AW 500 Molecular sieve @120 deg autoclave ref 66 | 0 | 38.5844 | 6.5352 | 27.1244 | 9.7792 | 0.6821 | 38.0479 | 0 |
| ST1X Carbon @ 80 deg autoclave ref 65 | 0 | 93.6399 | 0 | 27.304 | 77.6009 | 0 | 250.1089 | 0 |
| ST1X Carbon @ 80 deg autoclave ref 66 | 0 | 43.5858 | 0 | 28.0388 | 78.8577 | 0 | 256.46 | 0 |
| ST1X Carbon @ 120 deg autoclave ref 65 | 0 | 99.3595 | 0 | 25.7188 | 74.9626 | 0 | 239.8486 | 0 |
| ST1X Carbon @ 120 deg autoclave ref 66 | 0 | 48.7522 | 0 | 27.7375 | 72.7737 | 0 | 242.8736 | 0 |
| Mol sieve/Carbon @ 80 deg autoclave ref 65 | 0 | 47.5807 | 0 | 26.224 | 36.0314 | 0 | 140.276 | 0 |
| Mol sieve/Carbon @ 80 deg autoclave ref 66 | 0 | 38.0292 | 0 | 25.7825 | 35.3323 | 0 | 139.7663 | 0 |
| Mol sieve/Carbon @ 120 deg autoclave ref 65 | 0 | 46.2215 | 0 | 26.1542 | 37.4035 | 0 | 145.5055 | 0 |
| Mol sieve/Carbon @ 120 deg autoclave ref 66 | 0 | 35.5752 | 0 | 26.5073 | 35.9233 | 0 | 149.4047 | 0 |

| | Feed Impurity | | | | | | | |
|---|---|---|---|---|---|---|---|---|
| | 1122 | 31 | 133a | 32 | 125 | 12 | 263fb | 23 |
| | Feed Impurity level ppm wt/wt | | | | | | | |
| | 0.6197 | 10.6993 | 3.0693 | 0 | 0 | 0 | 0 | 0 |
| Stability test—Impurity levels post experiment | | | | | | | | |
| AW 500 Molecular sieve @ 80 deg autoclave ref. 65 | 0 | 0 | 1.222 | 94.4952 | 5.3457 | 26.304 | 14.7591 | |
| AW 500 Molecular sieve sieve @ 80 deg autoclave ref 66 | 0 | 0 | 0 | 0.5372 | 0 | 0 | 0 | 3.5424 |
| AW 500 Molecular sieve@ 120 deg autoclave ref 65 | 0 | 0 | 0 | 0 | 0 | 0 | 0 | 0 |
| AW 500 Molecular sieve @120 deg autoclave ref 66 | 0 | 0 | 0 | 0 | 0 | 0 | 0 | 0 |
| ST1X Carbon @ 80 deg autoclave ref 65 | 0 | 0 | 0 | 24.9735 | 0 | 0 | 0 | 0 |
| ST1X Carbon @ 80 deg autoclave ref 66 | 0 | 0 | 0 | 17.8747 | 0 | 0 | 0 | 0 |
| ST1X Carbon @ 120 deg autoclave ref 65 | 0 | 0 | 0 | 19.3595 | 0 | 7.7045 | 0 | 0 |
| ST1X Carbon @ 120 deg autoclave ref 66 | 0 | 0 | 0 | 15.9942 | 0 | 17.7729 | 0 | 0 |
| Mol sieve/Carbon @ 80 deg autoclave ref 65 | 0 | 0 | 0 | 1.8649 | 0 | 0 | 0 | 0 |
| Mol sieve/Carbon @ 80 deg autoclave ref 66 | 0 | 0 | 0 | 1.0693 | 0 | 0 | 0 | 0 |
| Mol sieve/Carbon @ 120 deg autoclave ref 65 | 0 | 0 | 0 | 0 | 0 | 4.7912 | 0 | 0 |
| Mol sieve/Carbon @ 120 deg autoclave ref 66 | 0 | 0 | 0 | 1.5667 | 0 | 0 | 0 | 0 |

-continued

| | 80 Deg C. | | | 120 Deg C. | | |
|---|---|---|---|---|---|---|
| | Mass material tested/g | Mass Change/g | % wt Change | Mass material tested/g | Mass Change/g | % wt Change |
| AW 500 | 20.0274 | +0.2066 | 1.54 | 20.0975 | −0.1143 | −0.57 |
| Molecular Sieve | 20.081 | +0.1498 | 1.94 | 20.0589 | −0.0940 | −0.47 |
| ST1X Carbon | 20.0156 | +0.3912 | 1.95 | 20.127 | +0.6425 | 3.19 |
| | 20.0086 | +0.3562 | 1.78 | 20.0141 | +0.8135 | 4.06 |
| 50/50 | 20.0225 | +0.4457 | 2.22 | 20.0337 | −0.1499 | −0.75 |
| AW500/ST1X | 20.073 | +0.4964 | 2.47 | 20.0511 | +0.4672 | 2.33 |

Example 4

The process of the invention was operated at commercial scale to remove trace impurities from a 180 kg batch of R-1243zf. An 85-liter adsorption bed was charged with 19.5 kg ST1x carbon and 19.5 kg AW500 molecular sieve. The Rig was sealed and evacuated to remove air. The feed vessels (total volume 270-liters) were charged with c.a. 180 kg of commercially available R-1243zf. This material contained similar impurities at similar levels to those specified in example 2.

The crude R-1243zf was then pumped from the feed vessels up through the adsorption bed and back into the feed vessels at ambient temperature. The R-1243zf charged was recirculated in this manner through the adsorption bed for a period of 5 hours. After which period the R-1243zf was pumped to a receiver vessel where it could be recovered for storage and analysis. After analysis each 180 kg charge was split into 60 kg batches. It was found that the adsorbent charge was capable of processing at least 360 kg of R-1243zf. The analysis of three 60 kg batches of R-1243zf processed in this manner are, presented in the Table below:

| Impurity | Impurity Level before treatment (ppm wt/wt) | Impurity Level after treatment—Batch 1 (ppm wt/wt) | Impurity Level after treatment—Batch 2 (ppm wt/wt) | Impurity Level after treatment—Batch 3 (ppm wt/wt) |
|---|---|---|---|---|
| 1225zc | 22 | ND | ND | ND |
| 1234yf | 24 | 29 | 26 | 30 |
| 134 | 77 | ND | 4.0 | 11 |
| Z-1225ye | 4.9 | 2.5 | 3.5 | 3.6 |
| 152a | 246 | 1.1 | 6.7 | 18 |
| 40 | 3.1 | ND | ND | ND |
| 31 | 11 | ND | ND | ND |
| Total 1243zf | 99.959 | 99.992 | 99.986 | 99.991 |

The invention is defined by the following claims.

The invention claimed is:

1. A process for removing one or more undesired (hydro)halocarbon compounds from a hydrofluoroalkene, the process comprising contacting a composition comprising the hydrofluoroalkene and one or more undesired (hydro)halocarbon compounds with activated carbon, wherein the hydrofluoroalkene is free of a $=CF_2$ moiety wherein at least one (hydro)halocarbon is selected from the group consisting of (hydro)fluoroalkanes, (hydro)fluoroalkenes, (hydro)fluoroalkynes and (hydro)chlorofluorocarbon (CFC) species.

2. The process according to claim 1 wherein the hydrofluoroalkene is a $C_{3-7}$ hydrofluoroalkene.

3. The process according to claim 2 wherein the $C_{3-7}$ hydrofluoroalkene is a hydrofluoropropene.

4. The process according to claim 3 wherein hydrofluoropropene is a trifluoropropene or a tetrafluoropropene.

5. The process according to claim 4 wherein the trifluoropropene is 3,3,3-trifluoropropene (R-1243zf).

6. The process according to claim 4 wherein the tetrafluoropropene is E/Z-1,3,3,3-tetrafluoropropene (R-1234ze) or 2,3,3,3-tetrafluoropropene (R-1234yf).

7. The process according to claim 1 wherein said at least one (hydro)halocarbon is a (hydro)chlorofluoroalkane, a (hydro)chlorofluoroalkene, or a (hydro)chlorofluoroalkyne.

8. The process according to claim 1 further comprising the step of contacting the composition with an aluminum-containing adsorbent.

9. The process according to claim 8 wherein the aluminium-containing absorbent is porous and comprises alumina or aluminosilicate.

10. The process according to claim 9 wherein the alumina comprises acidic functionality.

11. The process according to claim 9 wherein the aluminosilicate is a molecular sieve (zeolite) having pore sizes in the range 3 to 12 Angstroms.

12. The process according to claim 1 wherein the activated carbon is impregnated with an additive selected from a metal, a metal compound, a base and a mixture thereof.

13. The process according to claim 12 wherein the additive is an alkali metal salt.

14. The process according to claim 13 wherein the alkali metal salt is a base.

15. The process according to claim 1 wherein the or each undesired (hydro)halocarbon compound is present in an amount of from about 0.1 to about 1000 ppm, based on the weight of the composition comprising the hydrofluoroalkene and one or more undesired (hydro)halocarbon compounds.

16. The process according to claim 15 wherein the or each undesired (hydro)halocarbon compound is present in an amount of from about 0.1 to about 500 ppm.

17. The process according to claim 1 wherein following the contacting step, the resulting composition comprises the hydrofluoroalkene and from about 0 to about 10 ppm of the or each undesired (hydro)halocarbon compounds.

18. The process according to claim 17 wherein following the contacting step, the resulting composition comprises the hydrofluoroalkene and from about 0.01 to about 5 ppm of the or each undesired (hydro)halocarbon compounds.

19. The process according to claim 1 wherein the composition comprising the hydrofluoroalkene and one or more undesired (hydro)halocarbon compounds is a product stream from a process for producing the hydrofluoroalkene.

20. The process for removing one or more undesired (hydro)halocarbon compounds from a hydrofluoroalkene according to claim 19, which process is combined with one or more additional purification steps selected from the group consisting of distillation, condensation, phase separation, scrubbing with water, scrubbing with an aqueous base, and scrubbing with a mixture of water and an aqueous base.

21. The process according to claim 1 wherein the (hydro)fluoroalkyne is trifluoromethylacetylene (TFMA).

22. The process according to claim 1 wherein the activated carbon has a surface area of from about 100 to about 2000 m2.

23. The process according to claim 22 wherein the activated carbon has a surface area of from about 200 to about 1500 m2.

24. The process according to claim 1 wherein at least 50% of the undesired (hydro)halocarbon compound present in the composition is removed therefrom.

25. The process according to claim 24 wherein at least 70% of the undesired (hydro)halocarbon compound present in the composition is removed therefrom.

26. The process according to claim 25 wherein at least 90% of the undesired (hydro)halocarbon compound present in the composition is removed therefrom.

27. The process according to claim 1 wherein the process is conducted at from about −50° C. to about 200° C.

28. The process according to claim 27 wherein the process is conducted at from about 0° C. to about 100° C.

29. The process according to claim 28 wherein the process is conducted at from about 10° C. to about 50° C.

* * * * *